United States Patent [19]

Gatling et al.

[11] Patent Number: 4,814,448

[45] Date of Patent: Mar. 21, 1989

[54] PROCESS FOR PREPARING PHOSPHOROTHIOATES AND PHOSPHATES

[75] Inventors: Sterling C. Gatling; Karl L. Krumel, both of Midland, Mich.

[73] Assignee: The Dow Chemical Company, Midland, Mich.

[21] Appl. No.: 22,459

[22] Filed: Mar. 6, 1987

Related U.S. Application Data

[63] Continuation-in-part of Ser. No. 715,552, Mar. 25, 1985, abandoned.

[51] Int. Cl.$^4$ ............ C07F 9/58; C07F 9/65; C07F 9/09
[52] U.S. Cl. ............ 546/25; 544/243; 544/337; 558/162; 558/190; 558/192; 558/193; 558/196; 558/197; 558/206; 558/210; 558/211; 558/212; 558/215
[58] Field of Search ............ 558/162, 190, 192, 193, 558/196, 197, 206, 210, 211, 212, 215; 546/25, 243, 337

[56] References Cited

U.S. PATENT DOCUMENTS

| 3,907,815 | 9/1975 | Kroposki et al. | 546/25 |
| 3,917,621 | 11/1975 | Kroposki et al. | 546/25 |
| 3,928,370 | 12/1975 | Wang et al. | 546/25 |
| 3,972,887 | 8/1976 | Freedman | 546/25 |
| 4,007,197 | 2/1977 | Freedman et al. | 546/25 |
| 4,092,312 | 5/1978 | Kroposki et al. | 544/243 |
| 4,094,873 | 6/1978 | Kroposki et al. | 544/243 |
| 4,096,210 | 6/1978 | Freedman et al. | 558/98 |
| 4,147,866 | 4/1979 | Freedman et al. | 544/243 |

FOREIGN PATENT DOCUMENTS 6809749  7/1968  Netherlands ......... 546/193

OTHER PUBLICATIONS

Krishnakumar, V. K.; Synthetic Communications; 14(2); pp. 189–196 (1984).

Primary Examiner—Alan L. Rotman
Attorney, Agent, or Firm—S. Preston Jones; Ronald G. Brookens

[57] ABSTRACT

Certain phenyl and N-heterocyclic phosphorothioates and phosphates are prepared by the reaction of an appropriate alkali metal or alkaline earth metal -O-phenyl or N-heterocyclic compound with an appropriate phosphorochloridate or phosphorochloridothioate under alkaline conditions in a liquid reaction medium and in the presence of a tertiary amine catalyst and a nonionic surfactant having a HLB Value of from about 2.5 to about 20 or more.

12 Claims, No Drawings

PROCESS FOR PREPARING PHOSPHOROTHIOATES AND PHOSPHATES

RELATIONSHIP TO PRIOR APPLICATION

This application is a continuation-in-part of application Ser. No. 715,552 filed Mar. 25, 1985, now abandoned.

BACKGROUND OF THE INVENTION

The O-pyridyl phosphates and phosphorothioates were described by Rigterink in U.S. Pat. No. 3,244,586. Such compounds are particularly useful as insecticides and biocides. They are represented by Formula (I)

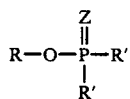   (I)

wherein
R represents halopyridyl,
Z represents oxygen or sulfur and each R' independently represents lower alkyloxy, amino or lower alkylamino.

Rigterink disclosed several methods for preparing the compounds but his preferred method comprised reacting a phosphorochloridate or phosphorochloridothioate of Formula (II)

   (II)

with an alkali metal or tertiary amine salt of a halopyridinol having the formula R—O-alkali metal or R—OH tertiary amine. The disclosed methods were carried out in an inert organic liquid under anhydrous conditions. In each of the disclosed processes, an alkali metal chloride or the tertiary amine hydrochloride salt is produced as a reaction by-product which is removed by filtration. The disclosure of U.S. Pat. No. 3,244,586 is incorporated herein by reference.

Other phosphorothioates and phenylphosphonothioates have been similarly prepared and used. See, for example, U.S. Pat. Nos. 4,007,197 and 4,147,866 both of which teach the reaction of an alkali metal phenate, pyridinate or pyrimidinate with an O,O-dialkylphosphorochloridothioate or O-alkyl phenylphosphonochloridothioate under alkaline conditions in a liquid reaction medium and in the presence of a co-catalyst mixture of a quaternary ammonium or phosphonium salt and a tertiary amine.

U.S. Pat. No. 3,928,370 teaches the preparation of dialkyl pyridylphosphates by the reaction of an alkali metal pyridinate and a dialkyl hydrogen phosphite in the presence of a liquid reaction medium and in the presence of a tertiary amine catalyst.

Many other commercially available phosphorothioates and phosphates prepared by the same general procedure as set forth above are listed in articles by O. Johnson in Chemical Week, pages 10–46 (July 26, 1972), and by E.E. Kenaga and W. E. Allison in the Bulletin of the Entomological Society of America, Volume 15, No. 2, pages 85–148 (June 1969) which also list the U.S. Patent Numbers of many of said compounds. These articles are incorporated herein by reference thereto.

SUMMARY OF THE INVENTION

The present invention is directed to the preparation of certain phosphorothioates and phosphates in high yields and of high purity. The compounds prepared in the present invention correspond to the general formulae

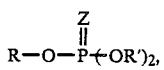   (III)

wherein:

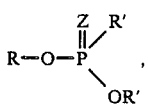   (IV)

or

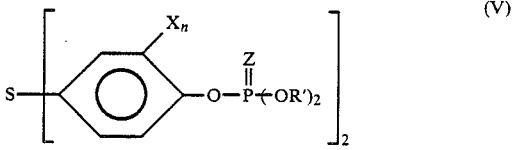   (V)

wherein:

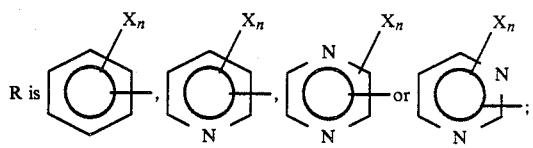

each R' independently represent alkyl of 1 to 6 carbon atoms, phenyl or pyridyl;
each X independently represent bromo, chloro, fluoro, iodo, —NR$^2$R$^3$ wherein R$^2$ and R$^3$ independently represent hydrogen and alkyl of 1 to 6 carbon atoms, cyano, nitro, alkyl of 1 to 6 carbon atoms, alkoxy of 1 to 6 carbon atoms, alkylthio of 1 to 6 carbon atoms or alkylsulfinyl of 1 to 6 carbon atoms;
n is 0, 1, 2 or 3 with the proviso, that when n is more than one, all substituents are sterically compatible with each other; and
Z is oxygen or sulfur.

An advantage of the present invention is the production of the above-indicated products in high yields and in high purity with reduced amounts of the by-product tetraethyl dithiopyrophosphate, also known as sulfotepp.

In the present specification and claims, the term "alkyl of 1 to 4 carbon atoms" is employed to designate straight chain alkyls of 1 to 6 carbon atoms, branched chain alkyls of 3 to 6 carbon atoms and cyclic alkyls of 3 to 6 carbon atoms such as, for example, methyl, ethyl, propyl, butyl, isopropyl, isobutyl, secondary butyl, tertiary butyl, cyclopropyl, cyclobutyl, amyl and cyclo.

In the present specification and claims, the terms "alkoxy of 1 to 4 carbon atoms," "alkylthio of 1 to 4 carbon atoms," "alkylsulfinyl of 1 to 4 carbon atoms" and "alkylsulfonyl of 1 to 4 carbon atoms" are employed to designate alkoxy and alkylthio groups of the formula

wherein Y is oxygen, sulfur, sulfinyl or sulfonyl and alkyl is defined as hereinabove set forth for "alkyl of 1 to 6 carbon atoms."

In the present specification and claims, the term "sterically compatible" is employed to designate X substituent groups which are not affected by steric hindrance as defined in The Condensed Chemical Dictionary, 7th Edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in Organic Chemistry of D. J. Cram and G. Hammon, 2nd Edition, McGraw-Hill Book Co., N.Y., page 215 (1964).

In the process of the present invention, the compounds of Formulae III, IV and V are prepared by reacting under alkaline conditions at a pH of from about 7 to about 13 substantially equimolar amounts of a compound corresponding to one of the formulae $$R-O^{\ominus}M^{\oplus} \quad (VI)$$

or

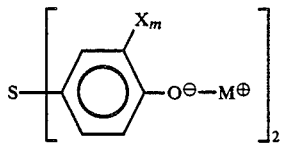

(VII)

with a phosphorochloridate or phosphorochloridothioate of one of the formulae

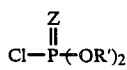

(VIII)

or

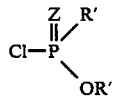

(IX)

in the presence of an aqueous solvent system comprising from about 1 part water and from about 0.1 to about 1 part of a hydrocarbon or chlorinated hydrocarbon solvent. In the above formulae, R, R', X, M and Z are as hereinbefore defined and M represents alkali metal or alkaline earth metal. In order to ensure a complete reaction, it is desirable to use an excess of the VI or VII reactant. The reaction is also carried out in the presence of a catalytic amount of a tertiary amine catalyst and a nonionic surfactant having a hydrophilic-lipophilic balance value (HLB) in the range of from about 1 to about 20 or more. Surfactants with HLP values of 5-15 are preferred.

In carrying out this reaction, the phenate, pyridinate and pyrimidinate salt reactant and the phosphorochloridate or phosphorochloridothioate reactant are mixed and contacted together in any convenient fashion, and the resulting mixture maintained for a period of time at a temperature in the range of from about 0° to about 100° C. to complete the reaction. The reaction is usually conducted under reflux conditions.

The term "alkali metal" is employed herein to represent sodium, potassium, rubidium, lithium and cesium. The term "alkaline earth metal" is employed herein to represent calcium, strontium, barium, radium, and magnesium.

The tertiary amines are used in the instant process in small but catalytic amounts. For example, amounts of from about 0.05 to about 5 mole percent, based on the alkali metal or alkaline earth metal phenate, pyridinate or pyrimidate reactant are suitable, but amounts of from about 0.1 to about 1.0 mole percent are generally preferred. Examples of suitable tertiary amines include aliphatic trihydrocarbyl amines (e.g. trimethylamine, ethyldimethylamine, butyldimethylamine, N,N,N',N'-tetramethylethylenediamine, and the like); aliphatic heterocyclic amines (e.g. 1-azabicyclo[2.2.2]octane, 1-methyl-2-imidazoline, 1-methylpyrrolidine, and the like); mixed aliphatic/aromatic amines (e.g. 4-(N,N-dimethylamino)pyridine, 4-(N-pyrrolidino)pyridine, phenyldimethylamine, and the like); and others like organic, sterically unhindered, nucleophilic, tertiary amines.

Suitable inert organic liquids which are employed as a part of the two-phase solvent system include, for example, hydrocarbon solvents (e.g. benzene, toluene, xylene, cyclohexane, etc.), chlorinated hydrocarbon solvents (e.g. methylene chloride, chloroform, carbon tetrachloride, tetrachloroethylene, etc.) and the like.

Representative surfactants having a hydrophilic lipophilic balance value (HLB) in the range of from about 1.0 to about 20 or more include PG 26-2, PG 59-13, Brij ®97, Atlox ®3434E, Atmos ®300 and the calcium salt of dodecylbenzene sulfonic acid (defined hereinafter). Other known surfactants meeting this criteria and which are useful in carrying out the present invention are taught in McCutcheon's Detergents and Emulsifiers, North American Edition, 1983 Annual; McCutcheon Division, McPublishing Co., 175 Rock Road, Glen Rock, N.J. 07452. The listed surfactants include condensation products of alkylene oxides with organic acids, polyoxyethylene derivatives of sorbitan esters, complex ether alcohols and the like. The surfactant is employed in amounts of from about 0.01 to about 5.0 weight percent, based on the reactants. It is generally preferred to use the surfactant in amounts of from about 0.05 to about 2.0 weight percent.

The alkaline conditions under which this reaction is carried out can be easily achieved by conducting the process in the presence of caustic (NaOH) or other conventional bases or by the use of an appropriate buffer system. The specific base employed is not critical and the only limitation on the base used is that it not unfavorably react with the reactants to prevent the desired reaction from taking place.

Agitation (e.g. stirring, swirling, etc.) of the reaction mixture is important, especially since this process is conducted in a 2-phase liquid reaction medium, (e.g. solvent and water).

The following examples illustrate the present invention and the manner by which it can be practiced but, as such, should not be construed as limitations upon the overall scope of the same.

EXAMPLE I

Preparation of O,O-diethyl O-(3,5,6-trichloro-2-pyridyl)phosphorothioate

Into a 700 ml baffled reactor equipped with a mechanical stirrer, a condenser, a dropping funnel, a thermometer and a pH probe were placed 99.7 grams (g) (0.419 mole) of sodium 3,5,6-trichloro-2-pyridinate hydrate, 105 milliliters (ml) of methylene chloride, 332 ml of water, 0.051 g (0.00419 mole (0.1 mole percent)) of 4-dimethylamino pyridine, 24.1 g of sodium, chloride, 3.0 g of sodium hydroxide and 1.05 g (1.0 weight percent) of polyglycol 26-2 surfactant (a proprietary material of The Dow Chemical Company, Midland, Mich., 48640; which is a reaction product of 1 mole of di-secondary butylphenol, 5 moles of ethylene oxide and 4 moles of propylene oxide).

The reaction mixture was heated to a reflux temperature of 39° C. while stirring at 1,000 RPM and 73.2 g (0.389 mole) of O,O-diethylphosphorochloridothioate was added as a single shot during 5 to 10 seconds. The reaction mixture was heated at a reflux temperature of 45° to 48° C. for 2 hours during which time the pH dropped from an initial value of 12.5 to a final value of 11.9.

The reaction mixture was filtered to remove excess sodium 3,5,6-trichloro pyridinate. The organic layer was separated from the aqueous layer and washed with 60 ml of water. The methylene chloride was then removed by heating under reduced pressure leaving 134.2 g (95.5 percent of theoretical) of the desired above-named product having a purity of 97 percent.

Following the procedure as outlined in Example I, changing only the surfactant and the amount of surfactant employed, the following yields and purity of the O,O-diethyl O-(3,5,6-trichloro-2-pyridyl)phosphorothioate product are obtained:

TABLE 1

| Surfactant Employed | Amount of Surfactant in Percent by weight of total reaction Mixture | HLB of Surfactant | Product Yield | Product Purity | Sulfotepp in Percent of Product |
| --- | --- | --- | --- | --- | --- |
| ATLOX ® 3434F[1] | 0.4 | >1 | 94.7 | 96.6 | 0.08 |
| Calcium salt of dodecylbenzene sulfonic acid | 0.7 | >20 | 92.4 | 96.3 | 0.10 |
| Calcium salt of dodecylbenzene sulfonic acid | 0.4 | >20 | 93.3 | 95.6 | 0.10 |
| Brij ® 97[2] | 1.0 | 12.4 | 92.5 | ~97 | 0.12 |
| ATMOS ® 300[3] | 1.0 | 2.8 | 94.8 | ~97 | 0.10 |
| PG 26-2 | 0.5 | 9.0 | 94.5 | 97 | 0.15 |
| " | 0.2 | 9.0 | 94.2 | 97 | 0.19 |
| PG 59-13[4] | 0.5 | 10–11 | 96.2 | 97.7 | 0.08 |

[1]Proprietary formulated material of ICI Americas, Inc., Wilmington, Delaware, 19897; which is a nonionic/anionic material.
[2]Proprietary material of ICI Americas, Inc., Wilmington, Delaware 19897, which is a nonionic polyoxyethylene oleyl ether.
[3]Proprietary material of ICI Americas, Inc., Wilmington, Delaware 19897, which is a nonionic liquid prepared from mono and diglycerides of fat forming fatty acids.
[4]Proprietary material of The Dow Chemical Company, Midland, Michigan 48640 which is a condensation product of 8 moles of ethylene oxide and 1 mole of tridecylalcohol.

EXAMPLE II

Preparation of O,O-diethyl O-(3,5,6-trichloro-2-pyridyl)phosphorothioate

Into a one liter par bomb were placed 90.0 g (0.415 mole) of 2,3,5,6-tetrachloropyridine, 53.32 g (0.9521 mole) of potassium hydroxide, and 306 g (16.98 mole) of water. The bomb was sealed and the reaction mixture was stirred and heated to 160° C. at 80 psi for 30 minutes. After cooling, the potassium pyridinate reaction product was added to a 700 ml esterfication reactor as described in Example I followed by the addition of 105 ml of methylene chloride, 0.5 g (0.56 weight percent) of polyglycol 26-2, and 0.045 g (0.0004 moles) of 4-dimethylaminopyridine. The reaction mixture was then heated to a reflux temperature of 40° C. while stirring at 740 rpm and 78 g (0.414 moles) of O,O-diethylphosphorochloridothioate was added as a single shot over 5 to 10 seconds. The reaction mixture was heated to a reflux temperature of 48° C. for two hours during which time the pH dropped from 12.8 to 11.9. The reaction mixture was filtered to remove excess pyridinate. The organic layer was separated from the aqueous layer and washed with 60 ml of water. The methylene chloride was then removed by evaporation under reduced pressure leaving 141.5 g (94.6 percent of theoretical) of the above-named product having a purity of 96.9 percent and a sulfotepp concentration of 0.12 percent.

What is claimed is:

1. A process for preparing a compound corresponding to one of the formulae

(III)

(IV)

or

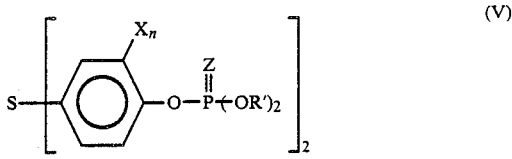

(V)

wherein:

R is 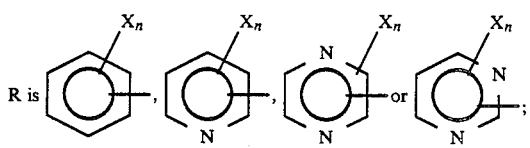

each R' independently represent alkyl of 1 to 6 carbon atoms, phenyl or pyridyl;

each X independently represent bromo, chloro, fluoro, iodo, cyano, nitro, alkyl of 1 to 6 carbon atoms, alkoxy of 1 to 6 carbon atoms, alkylthio of 1 to 6 carbon atoms or alkylsulfinyl of 1 to 6 carbon atoms or $-NR^2R^3$ wherein $R^2$ and $R^3$ independently represent hydrogen or alkyl of 1 to 6 carbon atoms;

n is 0, 1, 2 or 3 with the proviso that when n is more than one, all substituents are sterically compatible with each other; and Z is oxygen or sulfur which comprises reacting at a temperature of from about 0° to about 100° C., under alkaline conditions, substantially equimolar amounts of a compound (a) corresponding to one of the formulae

 (VI)

or

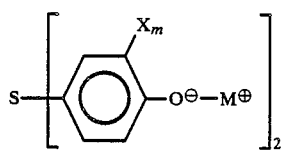 (VII)

with a compound (b) corresponding to one of the formulae

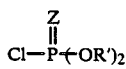 (VIII)

or

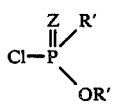 (IX)

wherein R, R', X, M and Z are defined and M represents an alkali metal or alkaline earth metal in the presence of an aqueous solvent system consists essentially of from about 1 part water and from about 0.1 to about 1 part of a hydrocarbon or chlorinated hydrocarbon solvent and in the presence of a nonionic surfactant having an HLB Value of from about 1 to about 20 and a catalytic amount of a tertiary amine.

2. The process as defined as claim 1 wherein the compound prepared corresponds to the formula

 (III)

3. The process as defined in claim 1 wherein the compound prepared corresponds to the formula

 (IV)

4. The process as defined in claim 1 wherein the compound prepared corresponds to the formula

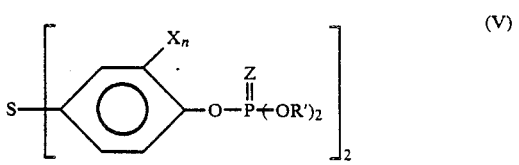 (V)

5. The process as defined in claim 2 wherein R is

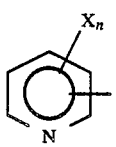

and R' is alkyl of 1 to 6 carbon atoms.

6. The process as defined in claim 5 wherein R is 3,5,6-trichloro-2-pyridinyl.

7. The process as defined in claim 6 wherein R' is methyl.

8. The process as defined in claim 6 wherein R' is ethyl.

9. The process as defined in claim 2 wherein the compound (a) is sodium O-3,5,6-trichloro-2-pyridinate and the compound (b) is O,O-diethylphosphorochloridothioate; said aqueous solvent system is a mixture of methylene chloride and water.

10. The process as defined in claim 9 wherein the nonionic surfactant is present in an amount of from about 0.05 to about 2.0 weight percent.

11. The process as defined in claim 2 wherein the compound (a) is potassium O-3,5,6-trichloro-2-pyridinate and the compound (b) is O,O-diethylphosphorochloridothioate; said aqueous solvent system is a mixture of methylene chloride and water.

12. The process as defined in claim 11 wherein the nonionic surfactant is present in an amount of from 0.05 to about 2.0 weight percent.

* * * * *